(12) United States Patent
Schmid et al.

(10) Patent No.: US 10,158,092 B2
(45) Date of Patent: *Dec. 18, 2018

(54) ORGANIC ELECTRONIC COMPONENT WITH DOPANT, USE OF A DOPANT AND METHOD FOR THE PRODUCTION OF THE DOPANT

(71) Applicant: OSRAM OLED GmbH, Regensburg (DE)

(72) Inventors: Guenter Schmid, Hemhofen (DE); Jan Hauke Wemken, Nuremberg (DE); Renate Kellermann, Erlangen (DE); Andreas Kanitz, Hoechstadt (DE); Benedict Hendrik Sandmann, Hunderdorf (DE)

(73) Assignee: OSRAM OLED GmbH, Regensburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/791,167

(22) Filed: Oct. 23, 2017

(65) Prior Publication Data

US 2018/0108849 A1    Apr. 19, 2018

Related U.S. Application Data

(63) Continuation of application No. 14/352,292, filed as application No. PCT/EP2012/070537 on Oct. 17, 2012, now Pat. No. 9,799,840.

(30) Foreign Application Priority Data

Oct. 17, 2011 (DE) .......................... 10 2011 084 639

(51) Int. Cl.
| | |
|---|---|
| H01L 51/54 | (2006.01) |
| H01L 51/00 | (2006.01) |
| H01L 51/50 | (2006.01) |
| C07F 1/00 | (2006.01) |
| C09K 11/06 | (2006.01) |
| H05B 33/14 | (2006.01) |

(52) U.S. Cl.
CPC .......... *H01L 51/0091* (2013.01); *C07F 1/005* (2013.01); *C09K 11/06* (2013.01); *H01L 51/002* (2013.01); *H01L 51/506* (2013.01); *H05B 33/14* (2013.01); *C09K 2211/188* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 3,970,649 A | 7/1976 | Bohler et al. | |
| 4,655,783 A | 4/1987 | Reinert et al. | |
| 5,741,623 A | 4/1998 | Mamba et al. | |
| 6,172,264 B1 | 1/2001 | Kobayashi et al. | |
| 6,410,166 B1 | 6/2002 | Takahashi et al. | |
| 6,833,202 B2 | 12/2004 | Lee et al. | |
| 7,234,417 B2 | 6/2007 | Laird | |
| 9,799,840 B2 * | 10/2017 | Schmid et al. | ..... H01L 51/0091 |
| 2002/0043663 A1 | 4/2002 | Seo et al. | |
| 2003/0059647 A1 | 3/2003 | Thompson et al. | |
| 2004/0180234 A1 | 9/2004 | Lee et al. | |
| 2010/0244009 A1 | 9/2010 | Parham et al. | |
| 2011/0315933 A1 | 12/2011 | Stoessel et al. | |
| 2012/0286254 A1 | 11/2012 | Stoessel et al. | |

FOREIGN PATENT DOCUMENTS

| | | |
|---|---|---|
| CN | 1633233 A | 6/2005 |
| CN | 101081889 A | 12/2007 |
| CN | 101747375 A | 6/2010 |
| DE | 102004046665 A1 | 7/2006 |
| DE | 102007053771 A1 | 5/2009 |
| DE | 102009013041 A1 | 9/2010 |
| DE | 102009057167 A1 | 6/2011 |
| JP | H07133281 A | 5/1995 |
| JP | 200283684 A | 3/2002 |
| JP | 201010691 A | 1/2010 |
| JP | 2011503886 A | 1/2011 |
| JP | 2012520241 A | 9/2012 |
| JP | 2013513225 A | 4/2013 |
| WO | 2003022007 A1 | 3/2003 |
| WO | 03095587 A1 | 11/2003 |
| WO | 2009062578 A1 | 5/2009 |
| WO | 2010000976 A2 | 1/2010 |
| WO | 2010102709 A1 | 9/2010 |
| WO | 2011063083 A1 | 5/2011 |
| WO | 2011066898 A1 | 6/2011 |

OTHER PUBLICATIONS

Chakraborty, L., et al., "Synthesis and properties of copper (II), oxovanadium (IV) and gadolinium (III) complexes derived from polar Schiff's bases," Journal of Molecular Structure, vol. 1002, Sep. 2011, pp. 135-144.

(Continued)

*Primary Examiner* — Marie R. Yamnitzky
(74) *Attorney, Agent, or Firm* — Slater Matsil, LLP

(57) ABSTRACT

An organic electronic component includes a substrate and a first electrode arranged on the substrate, and at least one organic functional layer arranged on the first electrode. The organic functional layer includes a matrix material into which a p-dopant has been introduced and a second electrode arranged on the organic functional layer. The p-dopant includes a copper complex having at least two ligands. Each ligand has a benzene unit with six carbon atoms. With respect to each ligand, an iminium group is linked directly as a substituent to one of the six carbon atoms of the benzene unit, and an oxygen is bound as a substituent to an adjacent carbon atom of the benzene unit, with the oxygen and the benzene unit together forming an aryloxy group. The ligands are coordinated to the copper cation, so that the copper complex has a trans-structure. The organic functional layer is hole-conducting.

10 Claims, 11 Drawing Sheets

(56) References Cited

OTHER PUBLICATIONS

Endo, J., et al., "Organic Electroluminescent Devices with a Vacuum-Deposited Lewis-Acid-Doped Hole-Injecting Layer," Japan Journal of Applied Physics, vol. 41, Mar. 15, 2002, pp. L358-L360.

Gao, W., et al., "Controlled p doping of the hole-transport molecular material N,N'-diphenyl-N,N'-bis(1-naphthyl)-1,1'-biphenyl-4,4'-diamine with tetrafluoroetracyanoquinodimethane," Journal of Applied Physics, vol. 94, No. 1, Jul. 1, 2003, pp. 359-366.

Harada, K., et al., "Organic Homojunction Diodes with a High Built-in Potential: Interpretation of the Current-Voltage Characteristics by a Generalized Einstein Relation," Physics Review Letters 94, Jan. 24, 2005, pp. 036601-1-036601-4.

He, G., et al., "High-efficiency and low-voltage p-i-n electrophosphorescent organic light-emitting diodes with double-emission layers," Applied Physics Letters, vol. 85, No. 17, Oct. 25, 2004, pp. 3911-3913.

He, G., et al., "Very high-efficiency and low voltage phosphorescent organic light-emitting diodes based on a p-i-n function," Journal of Applied Physics, vol. 95, No. 10, May 15, 2004, pp. 5773-5777.

Iglesias, A. L., et al., "New chiral Schiff base-Cu(II) complexes as cyclopropanation catalysts," Polyhedron, vol. 23, Sep. 6, 2004, pp. 3051-3062.

Kurata, T., et al, "Charge-Transporting Property of Polymer Films Doped with Organic Stable Radicals," Journal of Photopolymer Science and Technology, vol. 16, No. 2, May 28, 2003, pp. 297-298.

McKellar, J. R., "Electrical Conductivity of Some Organic Materials containing Metals," Discussions of the Faraday Society, Inorganic Chemisry Laboratory Oxford, vol. 51, Jan. 1, 1971, pp. 176-182.

Rayati, S., et al., "Electron-rich salen-type Schiff base complexes of Cu(II) as catalysts for oxidation of cyclooctene and styrene with tert-butylhydroperoxide: A comparison with electron-deficient ones," Inorganic Chemistry Communications, vol. 13, Nov. 18, 2009, pp. 203-207.

Tedim, J., et al, "Third-Order Nonlinear Optical Properties of DA-salen-Type Nickel(II) and Copper(II) Complexes," European Journal of Inorganic Chemistry, vol. 2006, Issue 17, Sep. 2006, pp. 3425-3433.

Zhou, X., et al., "Enhanced Hole Injection into Amorphous Hole-Transport Layers of Organic Light-Emitting Diodes Using Controlled p-Type Doping," Advanced Functional Materials, vol. 11, No. 4, Aug. 2001, pp. 310-314.

Zhou, X., et al., "High-efficiency electrophosphorescent organic light-emitting diodes with double light-emitting layers," Applied Physics Letters, vol. 81, No. 21, Nov. 18, 2002, pp. 4070-4072.

Zhou, X., et al., "Low-voltage inverted transparent vacuum deposited organic light-emitting diodes using electrical doping," Applied Physics Letters, vol. 81, No. 5, Jul. 29, 2002, pp. 922-924.

* cited by examiner

ORGANIC ELECTRONIC COMPONENT WITH DOPANT, USE OF A DOPANT AND METHOD FOR THE PRODUCTION OF THE DOPANT

CROSS-REFERENCE TO RELATED APPLICATIONS

This is a continuation application of U.S. application Ser. No. 14/352,292, filed on Apr. 16, 2014 and issued as U.S. Pat. No. 9,799,840 on Oct. 24, 2017 which is a national phase filing under section 371 of PCT/EP2012/070537, filed Oct. 17, 2012, which claims the priority of German patent application 10 2011 084 639.5, filed Oct. 17, 2011, each of which is incorporated herein by reference in its entirety.

TECHNICAL FIELD

An organic electronic component comprising a dopant is specified, as are a use of a dopant and a process for producing a dopant.

BACKGROUND

Factors that influence efficiency and lifetime of organic electronic components, for example, organic light-emitting diodes, include the quality of the charge carrier injection and the charge carrier transport. By means of doping, the conductivity of materials, and hence the charge carrier transport, can be increased by several orders of magnitude. The doping of organic materials with electron acceptors can, for example, increase the conductivity of hole conductor layers.

SUMMARY

One embodiment provides an organic electronic component having a novel dopant. A further embodiment provides a use of a novel dopant in a hole transport material. A further embodiment provides a process for producing a dopant.

BRIEF DESCRIPTION OF THE DRAWINGS

The invention is to be illustrated in detail by the figures and working examples. In the figures, identical elements are indicated by identical reference numerals. The figures should not be regarded as scale drawings.

DETAILED DESCRIPTION OF ILLUSTRATIVE EMBODIMENTS

Figure 1A:
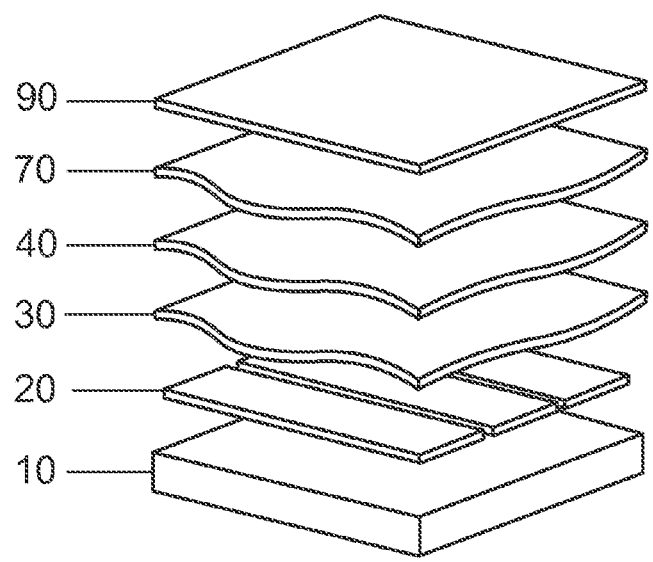
FIG. 1a shows the schematic three-dimensional view of an organic light-emitting diode.

An organic electronic component is described, comprising a substrate, a first electrode on the substrate, at least one organic functional layer comprising a matrix material into which a p-dopant has been introduced on the first electrode, and a second electrode on the at least one organic functional layer. This p-dopant comprises a copper complex having at least one ligand containing an aryloxy group and an iminium group.

"p-Dopant" in this context is understood to mean a dopant having electron acceptor properties, which can thus generate especially holes, i.e., positive charge carriers or missing electrons, for example, in a matrix material into which it may be embedded. The dopant increases the number of free charge carriers and hence the conductivity, which is a product of mobility and number of charge carriers. Assuming that the mobility stays the same, there is an increase in the conductivity on doping through the increase in the number of charge carriers.

"On" in connection with the arrangement of the elements of the component may be understood to mean either a direct arrangement or an indirect arrangement. Thus, two elements may be arranged one on top of another such that they encompass a common interface, or such that further elements are arranged between them.

"Copper complex" hereinafter shall be understood to mean an organometallic complex which contains a copper cation as the central atom, and at least one ligand. More particularly, the copper complex may have two ligands. The aryloxy group of the at least one ligand may be coordinated or bound to the copper cation by the oxygen atom present therein, and the iminium group by the nitrogen atom present therein. If two ligands are present in the copper complex, the copper cation may thus be coordinated or bound to two oxygen atoms and to two nitrogen atoms.

Such a component has a functional layer with optimized hole transport and, compared to the rest of the component, a minimized voltage drop and hence improved efficiency.

If the organic electronic component is an organic light-emitting diode, the p-dopant in the at least one functional layer may additionally influence the appearance of the light-emitting diode in the switched-off state (called the "off-state appearance"). The p-dopant is configured such that the color of the functional layer into which it has been introduced can be modified as a function of the concentration of the p-dopant without altering the electrical conductivity of the functional layer.

To date, organic light-emitting diodes have been configured in such a way that, for example, reddish hole conductor layers which absorb some blue and some green light are optically compensated such that the diodes in the switched-on state emit a pleasant white light. With the novel p-dopant, the light-emitting diode, even in the switched-off state, can be given a visual color impression when the functional layer, for example, adjoins a transparent electrode.

In one development, the aryloxy group and the iminium group of the ligand are a salicylaldiminate group. "Salicylaldiminate group" is understood to mean a ligand formed from a salicylaldehyde and an aromatic mono- or diamine or an olefinic mono- or diamine. Thus, the ligand comprises an amine-fused salicylaldehyde group and is capable of complexation between aryloxy group and the nitrogen of the iminium group, for example an azomethine group. Thus, p-dopants reduced in cost compared to p-dopants used to date are provided.

If the copper complex has two ligands of this kind, because of their structure, these may be coordinated to the copper cation such that the copper complex has a cis structure or a trans structure. The copper complex having cis structure can be converted to a copper complex having trans structure. By means of temperature, pressure and choice of solvent, the synthesis of the copper complex can be controlled such that one isomer, cis or trans structure, forms preferentially.

In addition, the copper cation in the copper complex may be present in the II oxidation state. The notation $Cu^{II}$ is therefore also used hereinafter.

In a further embodiment, the copper complex may have one of the general formulae I or II:

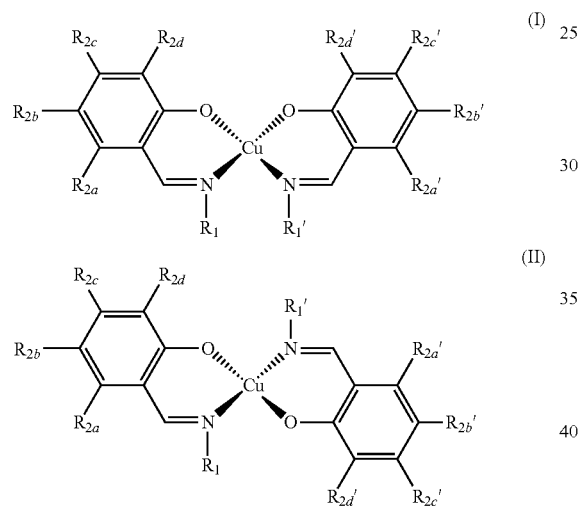

Formula (I) is a cis isomer of the copper complex, formula (II) a trans isomer. Such a copper complex thus contains two ligands coordinated or bound to the copper cation.

In the formulae (I) and (II): $R_1$, $R_{1'}$, $R_{2x}$ and $R_{2x'}$ (where each x represents a, b, c or d) are each independently selected from a group comprising unbranched, branched, fused, cyclic, unsubstituted and substituted alkyl radicals, substituted and unsubstituted aromatics, substituted and unsubstituted heteroaromatics.

Examples of such substituents are methyl groups, ethyl groups, decahydronaphthyl groups, cyclohexyl groups and alkyl radicals which or may be partly substituted and have up to 20 carbon atoms. These alkyl radicals may additionally contain ether groups such as ethoxy or methoxy groups, ester groups, amide groups, carbonate groups or else halogens, especially F.

Examples of substituted or unsubstituted aromatics are phenyl, diphenyl, naphthyl, phenanthryl or benzyl.

Examples of possible heteroatoms are shown in table 1 below. For the sake of simplicity, only the base structure of each of the heteroaromatics is shown. In principle, this base structure may be substituted by further R radicals which may be of a form analogous to the above-defined $R_1$, $R_{1'}$, $R_{2x}$ and $R_{2x'}$ radicals. The bond to the ligand may be at any bonding-capable site in the base structure.

TABLE 1

| Structure | Name |
|---|---|
| (furan structure) | Furan |
| (thiophene structure) | Thiophene |
| (pyrrole structure) | Pyrrole |
| (oxazole structure) | Oxazole |
| (thiazole structure) | Thiazole |
| (imidazole structure) | Imidazole |
| (isoxazole structure) | Isoxazole |
| (isothiazole structure) | Isothiazole |
| (pyrazole structure) | Pyrazole |
| (pyridine structure) | Pyridine |
| (pyrazine structure) | Pyrazine |

TABLE 1-continued
| | |
|---|---|
|  Pyrimidine | 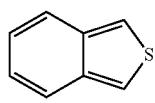 2-benzothiophene |
|  1,3,6 Triazine | 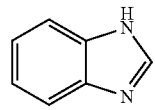 1H-benzimidazole |
|  Pyrylium | 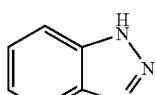 1H-benzotriazole |
| 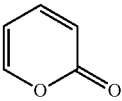 alpha-Pyrone | 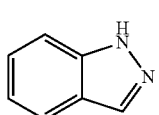 1H-indazole |
| 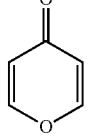 gamma-Pyrone | 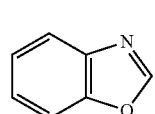 1,3-benzoxazole |
| 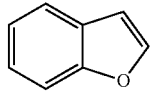 Benzo [b] furan | 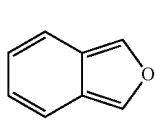 2-benzofuran |
| 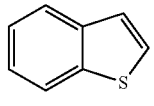 Benzo [b] thiophene | 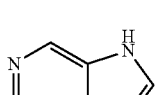 7H-purine |
| 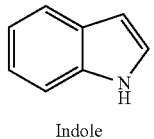 Indole | 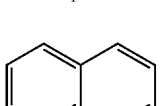 quinoline |
| 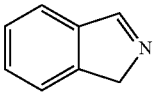 2H-Isoindole | 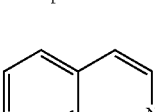 isoquinoline |
| 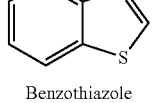 Benzothiazole | 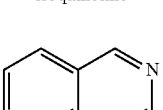 Quinazoline |

TABLE 1-continued

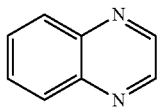

Quinoxaline

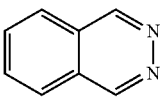

phthalazine

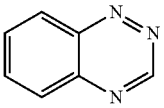

1,2,4-benzothiazine

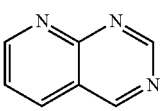

Pyrido[2,3-d]pyrimidine

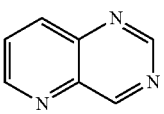

Pyrido[3,2-d]pyrimidine

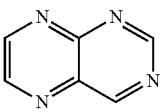

pteridine

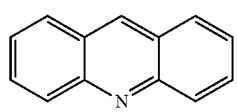

acridine

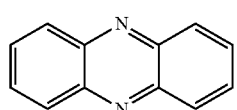

phenazine

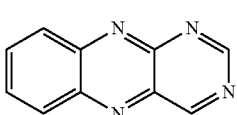

benzo[g]pteridine

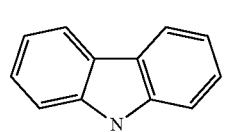

9H-carbazole

TABLE 1-continued

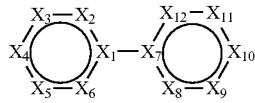

B pyridine & Derivate
(0-2X/Ring = N)

In addition, the substituents in the general formulae (I) and (II) in the two ligands may be the same or different. In one embodiment, $R_1$ and $R_{1'}$ and $R_{2x}$ and $R_{2x'}$ are each the same. If the substituents selected are the same, the synthesis of the copper complex is particularly simple to conduct, which also causes a reduction in costs.

In addition, $R_1$ and $R_{1'}$ may be joined to one another. Thus, a bridge may be formed between the two ligands coordinated or bound to the copper cation. Embodiments of this kind are shown in the general forms (Ia) and (IIa).

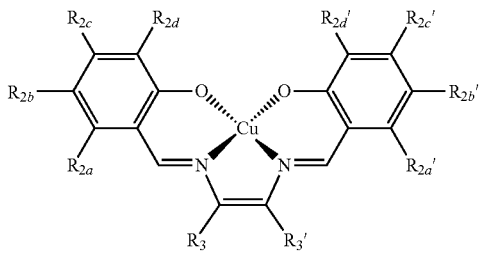

(Ia)

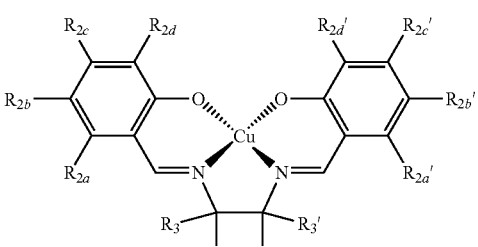

(IIa)

Formulae (Ia) and (IIa) are each cis isomers of the bridged copper complex. In principle, a bridge is also conceivable in trans isomers when an appropriately long bridge between $R_1$ and $R_{1'}$ is selected. For the $R_3$, $R_{3'}$, $R_4$ and $R_{4'}$ radicals, the definitions of the $R_1$, $R_{1'}$, $R_2$ and $R_{2'}$ radicals apply correspondingly.

Copper complexes having one of these general formulae (I), (Ia), (II) or (IIa), because of their Lewis acidity, can be used effectively as p-dopants, since they have electron-withdrawing ligands and hence their electron acceptor properties are enhanced. Thus, the hole conductivity in the organic functional layer of the organic electronic component is improved.

In a further embodiment, at least one of $R_1$, $R_{1'}$, $R_{2x}$ and $R_{2x'}$ and—if present—of $R_3$, $R_{3'}$, $R_4$ and $R_{4'}$ may have an electron-withdrawing substituent.

An electron-withdrawing substituent, for example, a fluorine atom F, may be present directly at the bonding carbon of at least one of the $R_1$, $R_{1'}$, $R_{2x}$ and $R_{2x'}$ radicals and—if present—of $R_3$, $R_{3'}$, $R_4$ and $R_{4'}$. Such a radical may have, for example, one of the general formulae (IIIa) or (IIIb):

(IIIa)

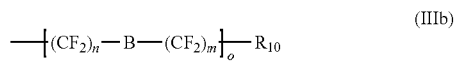

(IIIb)

In the formula (IIIa), n may be 1 to 20, $R_{10}$ may be a fluorine atom F. In one variant, n=2 and $R_{10}$=F. $R_{10}$ may also be selected in the same way as the $R_1$, $R_{2x}$, $R_3$ and $R_4$ radicals. Particular preference is given here to aliphatic chains and aromatics.

In formula (IIIb), n, m and o may each independently be 0 to 20; more particularly, n and m may be 2 and o may be selected within the range from 1 to 5. $R_{10}$ may be F and B may be O. Alternatively, B may also be selected from S, Se, NH, N—R, PH and P—R, where R may be selected as per $R_1$, $R_{2x}$, $R_3$ and $R_4$. Otherwise, $R_{10}$ may be selected in the same way as the $R_1$, $R_{2x}$, $R_3$ and $R_4$ radicals. Particular preference is given here to aliphatic chains and aromatics.

In addition, an electron-withdrawing substituent may also be present on an aromatic $R_1$, $R_{2x}$, $R_3$ or $R_4$ radical. Examples of such radicals are shown in the general formulae (IIIc) and (IIId):

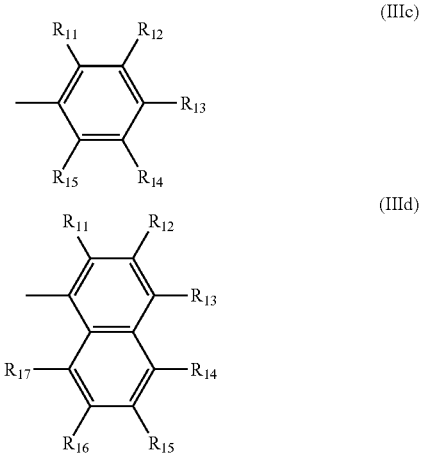

In the formulae (IIIc) and (IIId), $R_{11}$ to $R_{17}$ may each independently be selected from a group comprising H, F, $CF_3$, CN and $NO_2$. In addition, $R_{11}$ to $R_{17}$ may each independently be selected in the same way as the $R_1$, $R_{2x}$, $R_3$ and $R_4$ radicals. More particularly, they may comprise wholly or partly fluorinated systems.

Electron-withdrawing substituents in the $R_1$, $R_{2x}$, and—if present—$R_3$ and $R_4$ radicals may further enhance the hole-conducting character of the radicals, since they increase the electron-withdrawing action of the ligand, such that p-dopants having electron-withdrawing substituents in the ligands are particularly effective in increasing the electrical conductivity of the functional layer into which they have been introduced.

The at least one organic functional layer may be hole-conducting. For example, it may be a hole transport layer or a hole injection layer.

The matrix material of the functional layer may be a hole transport material comprising organic small molecules, polymers or mixtures thereof.

If the hole transport layer is selected from small molecules, these may be selected, for example, from a group comprising N,N'-bis(naphthalen-1-yl)-N,N'-bis(phenyl)-9,9-dimethylfluorene, N,N'-bis(3-methyl-phenyl)-N,N'-bis(phenyl)-9,9-diphenylfluorene, N,N'-bis(naphthalen-1-yl)-N,N'-bis(phenyl)-9,9-diphenyl-fluorene, N,N'-bis(naphthalen-1-yl)-N,N'-bis(phenyl)-2,2-dimethylbenzidine, N,N'-bis(3-methylphenyl)-N,N'-bis(phenyl)-9,9-spirobifluorene, 2,2',7,7'-tetrakis-(N,N-diphenylamino)-9,9'-spirobifluorene, N,N'-bis-(naphthalen-1-yl)-N,N'-bis(phenyebenzidine, N,N'-bis-(naphthalen-2-yl)-N,N'-bis(phenyl)benzidine, N,N'-bis-(3-methylphenyl)-N,N'-bis(phenyl)benzidine, N,N'-bis(3-methylphenyl)-N,N'-bis(phenyl)-9,9-dimethylfluorene, N,N'-bis(naphthalen-1-yl)-N,N'-bis(phenyl)-9,9-spirobifluorene, di-[4-(N,N-ditolylamino)phenyl]cyclo-hexane, 2,2',7,7'-tetra(N,N-ditolyl)aminospirobi-fluorene, 9,9-bis[4-(N,N-bisbiphenyl-4-ylamino)-phenyl]-9H-fluorene, 2,2',7,7'-tetrakis[N-naphthalenyl-(phenyl)amino]-9,9-spirobifluorene, 2,7-bis[N,N-bis-(9,9-spirobifluoren-2-yl)amino]-9,9-spirobifluorene, 2,2'-bis[N,N-bis(biphenyl-4-yl)amino]-9,9-spirobi-fluorene, N,N'-bis(phenanthren-9-yl)-N,N'-bis(phenyl)-benzidine, N,N,N',N'-tetranaphthalen-2-ylbenzidine, 2,2'-bis(N,N-diphenylamino)-9,9-spirobifluorene, 9,9-bis[4-(N,N-bis(naphthalen-2-yl)amino)phenyl]-9H-fluorene, 9,9-bis[4-(N,N'-bis(naphthalen-2-yl)-N,N'-bisphenylamino)phenyl]-9H-fluorene, titanium oxide phthalocyanine, copper phthalocyanine, 2,3,5,6-tetrafluoro-7,7,8,8-tetracyanoquinodimethane, 4,4',4"-tris(N-3-methylphenyl-N-phenylamino)triphenylamine,4,4',4"-tris(N-(2-naphthyl)-N-phenylamino)triphenyl-amine, 4,4',4"-tris(N-(1-naphthyl)-N-phenylamino)tri-phenylamine, 4,4',4"-tris(N,N-diphenylamino)triphenyl-amine, N,N'-di[(1-naphthyl)-N,N'-diphenyl]-1,1'-biphenyl]-4,4'-diamine, pyrazino[2,3-f][1,10]-phenanthroline-2,3-dicarbonitrile, N,N,N',N'-tetrakis-(4-methoxyphenyebenzidine, 2,7-bis[N,N-bis(4-methoxy-phenyl)amino]-9,9-spirobifluorene, 2,2'-bis[N,N-bis(4-methoxyphenyl)amino]-9,9-spirobifluorene, N,N'-di-(naphthalen-2-yl)-N,N'-diphenylbenzene-1,4-diamine,N,N'-diphenyl-N,N'-di[4-(N,N-ditolylamino)phenyl]-benzidine and N,N'-diphenyl-N,N'-di[4-(N,N-diphenylamino)phenyl]benzidine.

Polymeric hole transport materials may be selected from a group comprising PEDOT (poly(3,4-ethylene-dioxythiophene), PVK (poly(9-vinylcarbazole), PTPD (poly(N,N'-bis (4-butylphenyl)-N,N'-bis(phenyl)-benzidine), P3HT (poly (3-hexylthiophene) and PANI (polyaniline). These repeat units of these illustrative polymeric materials are shown in the formulae (IVa) to (IVe):

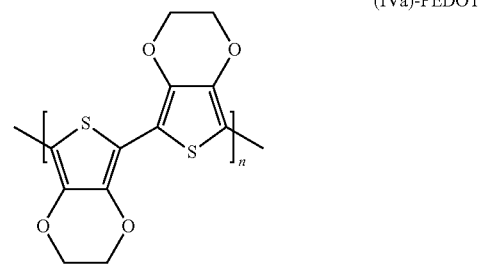

(IVa)-PEDOT

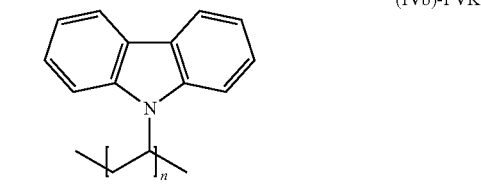

(IVb)-PVK

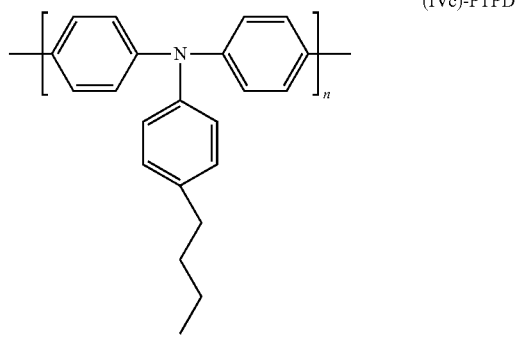

(IVc)-PTPD

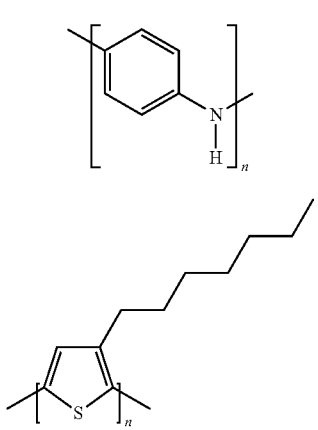
(IVd)-PANI (IVe)-P3HT

If a mixture of small molecules and polymeric hole transport materials is present, the mixing ratio may be between 0 and 100%.

The abovementioned p-dopants may be present in the matrix material with a concentration of 0.1 to 50% by volume, especially with a concentration of 2 to 30% by volume.

If an organic functional layer, for example, a hole transport layer, is produced, the materials, i.e., the matrix material in which the p-dopant has been embedded, may be deposited from the gas phase or from the liquid phase. If the matrix material contains small molecules, the deposition can be effected from the liquid phase or from the gas phase; if polymeric materials are selected, these can be deposited from the liquid phase. The film-forming properties in the production of the functional layer can be improved in the case of processing from the liquid phase when a mixture of small molecules and polymeric materials is used as the matrix material.

The solvents used for the deposition from the liquid phase may be organic solvents selected, for example, from a group comprising chlorobenzene, chloroform, toluene, THF and methoxypropyl acetate.

In one embodiment, molecules of the p-dopant may be coordinated by at least one molecule each of the matrix material. For example, the doping of the matrix material can be effected by virtue of coordination of one to two hole transport material molecules in the axial positions of the copper complex. The square-planar coordination environment of the dopant can thus be expanded through a tetragonal pyramid (one matrix material molecule) to an octahedron (two matrix material molecules). In principle, it is also possible that two dopant molecules are bridged via one bifunctional matrix material molecule.

Using the example of NPB (N,N'-di[(1-naphthyl)-N,N'-diphenyl]-1,1'-biphenyl)-4,4'-diamine) as matrix material and a schematic copper complex in which only the two bonds from the copper cation to the ligands are shown in each case, such a coordination is shown in scheme 1:

Scheme 1

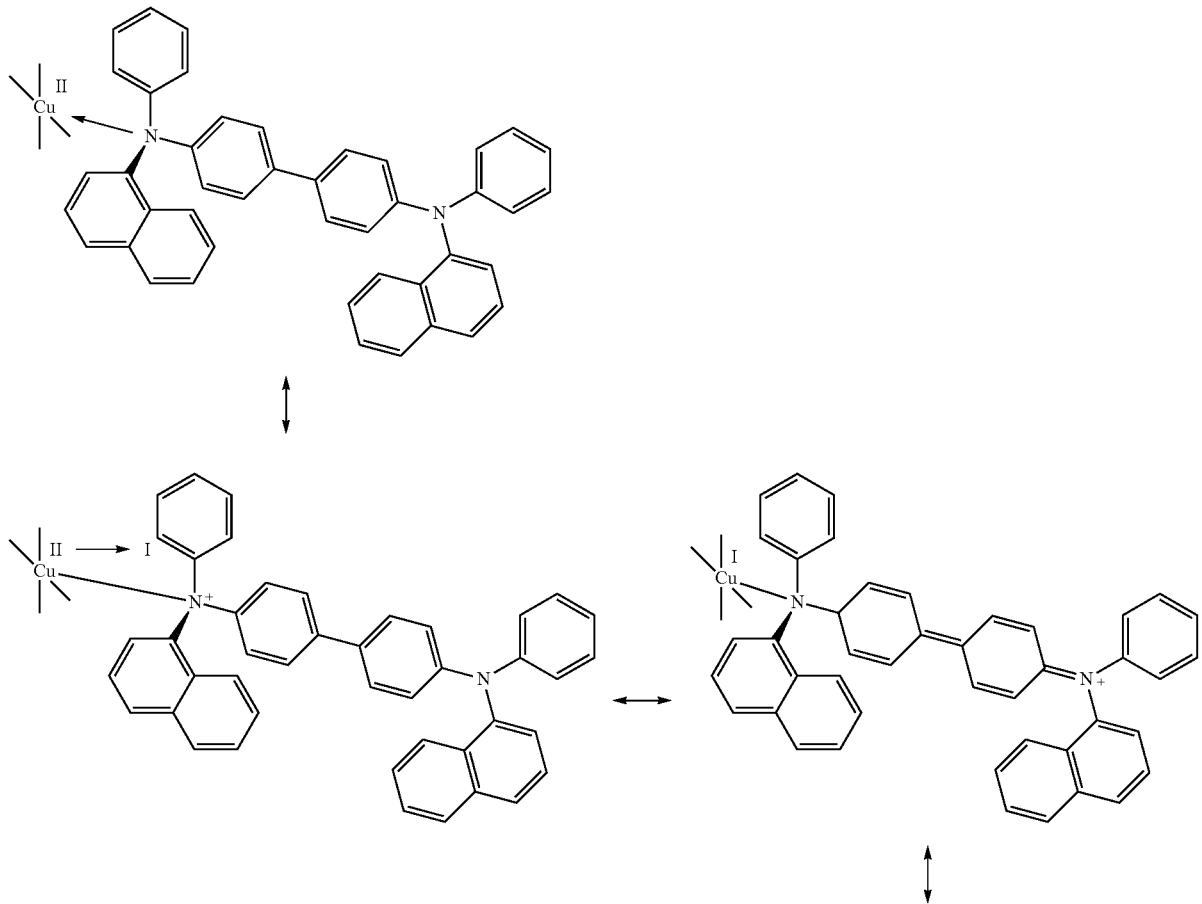

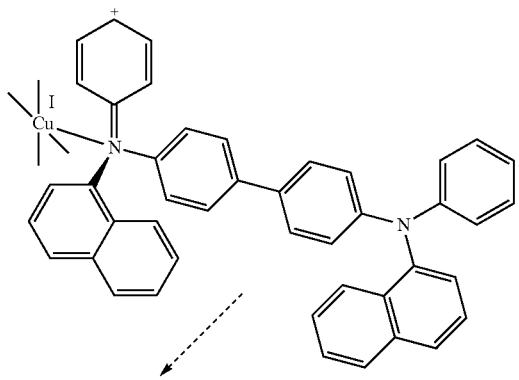

The coordination is effected via an interaction between the nitrogen atom of the NPB and the copper cation, such that a positive charge on the copper cation can be delocalized. This delocalization, which can also extend to other hole-transporting molecules, is shown by the four illustrative mesomeric structures in scheme 1, but these should be understood merely in a formal sense.

The component according to the above details may be selected from a group comprising field-effect transistors, solar cells, photodetectors, optoelectronic components, light-emitting diodes and displays. More particularly, the component may be an organic light emitting diode (OLED). The functional layer may, especially in OLEDs, take the form of a hole transport layer which may be arranged close to an electrode, for example, the anode, and/or of a hole-conducting partial layer of a charge-generating layer sequence (charge generation layer, CGL).

A charge-generating layer sequence may be understood to mean a combination of adjacent n- and p-doped organic partial layers. By means of a charge-generating layer sequence, it is possible to connect mutually adjacent organic functional stacks to one another, each of which may contain, for example, functional layers and emitting layers, in which case the charge-generating layer sequence can inject charge carriers into the adjacent organic functional stacks.

By virtue of the components comprising a p-dopant according to the above details, they are less expensive to produce and have optimized charge transport. Overall, the component can thus have improved efficiency and lifetime. In the case of OLEDs, it is additionally possible to modify the appearance in the switched-off state through the use of the p-dopant, such that the OLED no longer has a gray appearance, as is conventional, but gives a colored impression to an outside observer.

Additionally specified is the use of a copper complex having at least one ligand containing an aryloxy group and an iminium group as a p-dopant in a hole transport material. More particularly, the copper complex may have one of the general formulae I and II:

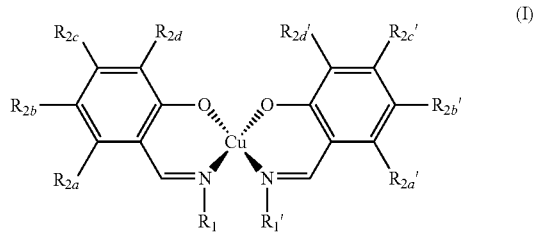

(I)

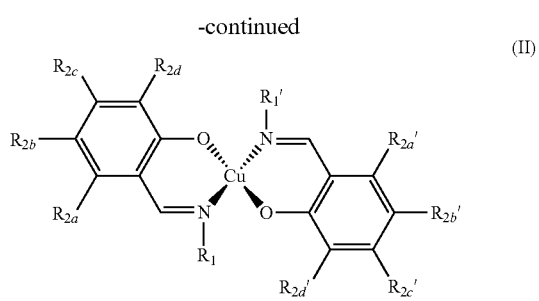

(II)

where
$R_1$, $R_{1'}$, $R_{2x}$, $R_{2x'}$ where x=a, b, c or d are each independently selected from a group comprising unbranched, branched, fused, cyclic, unsubstituted and substituted alkyl radicals, substituted and unsubstituted aromatics, substituted and unsubstituted heteroaromatics.

In further embodiments, the copper complex may be configured analogously to the details given in relation to the p-dopant present in the organic electronic component. The hole transport materials selected, in which the p-dopant is used, may, for example, be the hole transport materials mentioned in relation to the organic electronic component.

The use of such a copper complex as p-dopant in hole transport materials increases the conductivity thereof by multiple orders of magnitude. This is brought about at least partly by the Lewis acid properties thereof. In addition, the use of such a copper complex as p-dopant is particularly inexpensive, since the copper complex can be produced from inexpensive starting materials and by means of a process which is simple to conduct.

Additionally specified is a process for producing a p-dopant comprising a copper complex having at least one ligand containing an aryloxy group and an iminium group, in which the at least one ligand is synthesized and, at the same time, a copper cation is complexed. Such a process is firstly inexpensive because of the starting materials used and is secondly particularly simple to conduct.

The simultaneous synthesis of the ligand and of the complex can also be referred to as a template synthesis, which means that only a one-stage reaction has to be conducted in order to prepare ligand and the complex with the ligand. The same also applies to the preparation of copper complexes having more than one ligand.

In one embodiment of the process, a fluorinated or unfluorinated salicylaldehyde and a fluorinated or unfluorinated amine selected from a group comprising aromatic monoamines, olefinic monoamines, aromatic diamines and olefinic diamines is reacted with a copper salt. More particularly, a copper(II) salt can be used. Examples of copper(II) salts are $CuCl_2$, $CuBr_2$ or copper acetate. For purification, the compounds obtained can be sublimed.

Scheme 2 shows an embodiment of the process in which salicylaldehyde is reacted with an olefinic diamine and a copper salt to give a copper complex wherein the two ligands are bridged (route 1, above the reaction arrow) and with an olefinic monoamine and a copper salt to give a copper complex having two unbridged ligands (route 2, below the reaction arrow):

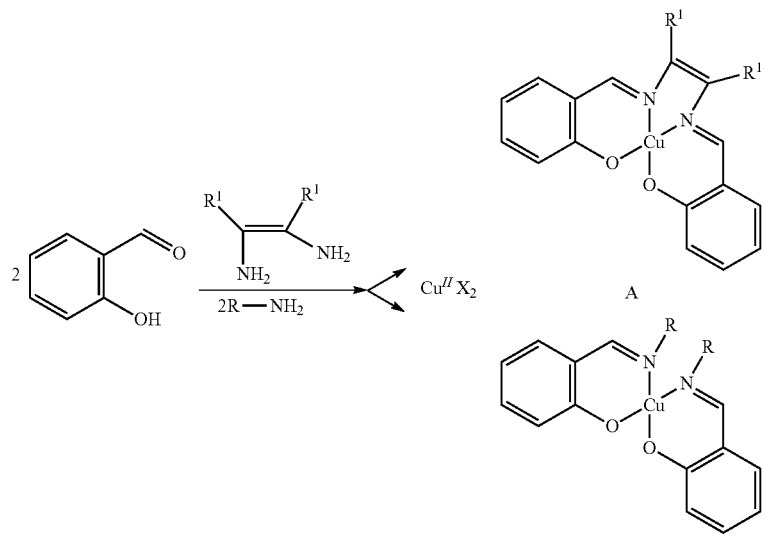

R and $R^1$ may be selected analogously to the $R_1$, $R_{2x}$ and, if present, $R_3$ and $R_4$ radicals specified above in relation to the p-dopant of the organic electronic component. The products obtained by route 1 and route 2 are indicated by A. $Cu^{II}X_2$ represents a copper salt which may be selected, for example, from $CuCl_2$, $CuBr_2$ and copper acetate.

The reaction proceeds spontaneously and is therefore easy to conduct.

FIGS. 1a) and 1b) show a schematic three-dimensional and a schematic two-dimensional side view of an OLED. A first electrode 20 has been applied to a substrate 10. FIG. 1a) indicates that this electrode may be structured. A hole injection layer 30 has been applied to the first electrode 20, and to the former a hole transport layer 40, an emission layer 50, which may comprise a host material and an emission material, a hole-blocking layer 60, an electron transport layer 70 and an electron injection layer 80. Finally, a second electrode 90, configured as a cathode in this example, has been applied. For the sake of clarity, FIG. 1a) does not show all the layers. An OLED need not contain all the layers between the first and second electrodes 20, 90. In addition, OLEDs according to FIGS. 1a) and 1b) may be stacked and be connected to one another via charge-generating layer sequences (not shown here).

Figure 1B:
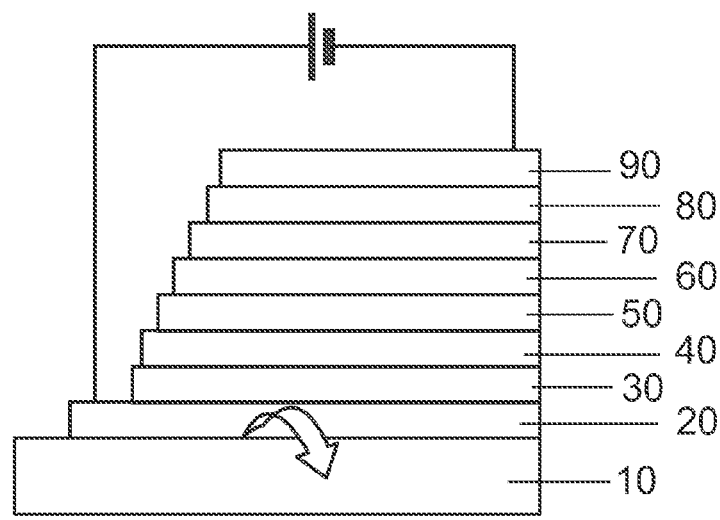
FIG. 1b shows the schematic side view of an organic light-emitting diode.

FIG. 1b) additionally shows that a voltage is applied between the first electrode 20 and second electrode 90. This leads to generation of excitons and hence to emission of electromagnetic radiation, especially within the visible wavelength range. The arrow in FIG. 1b) indicates the direction in which the radiation is emitted from the component. In this case, the radiation is emitted through the substrate 10. Through-emission from the second electrode 90 is likewise conceivable. It is also possible to achieve double-sided emission.

Illustrative materials for the layers shown in FIGS. 1a) and 1b) include glass for the substrate 10, ITO (indium tin oxide) or silicon for the first electrode 20, and aluminum for the second electrode 90. Further materials which can be used in the layers of an OLED are known to those skilled in the art and will therefore not be elucidated any further here.

Some working examples for syntheses of inventive copper complexes are specified hereinafter:

1) Copper(II) (N,N'-2,3-butene-1,4-dinitrile-2,3-diyl)-disalicylaldiminate (Referred to Hereinafter as K1)

A mixture of $Cu(CH_3COO)_2$ (0.04 mol; 7.99 g) and ethanol (300 ml) is initially charged and stirred while heating until all of the $Cu(CH_3COO)_2$ has dissolved. In a 2nd reaction mixture, the substances salicylaldehyde (0.021 mol; 2.63 g), diaminomaleonitrile (0.04 mol; 4.32 g) and ethanol (150 ml) are initially charged and likewise dissolved. After the two solutions have been combined and refluxed overnight, a reddish-black solid separates out, which is filtered off (crude product yield: 5.65 g, corresponding to 38%). The crude product is purified by recrystallization with DMF (300 ml) and subsequent precipitation with ethanol/diethyl ether.

The pure substance thus obtained is recrystallized once again with EtOH, dried and sublimed at 220° C. ($10^{-5}$ mbar).

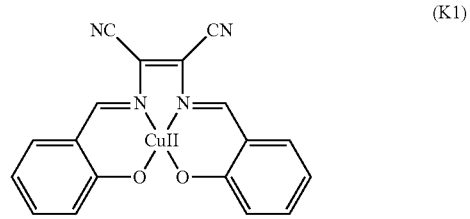
(K1)

2) Copper(II)-(bis-N,N'-4-tolyl)disalicylaldiminate
(Referred to Hereinafter as K2)

$Cu(CH_3COO)_2$ (0.0233 mol; 4.66 g) is dissolved in ethanol (120 ml). As a separate solution, p-toluidine (0.047 mol; 5 g) and salicylaldehyde (0.047 mol; 5.7 g) and ethanol (120 ml) are initially charged and dissolved. The two mixtures are combined and stirred at room temperature overnight. The suspension is concentrated a little and then the brown-black precipitate is filtered off and dried. The yield of crude product is 9.95 g (corresponding to 87.5%).

The substance (m.p. 205° C.) is sublimed at 180° C. ($10^{-5}$ mbar) and then once again at 170° C. ($10^{-5}$ mbar).

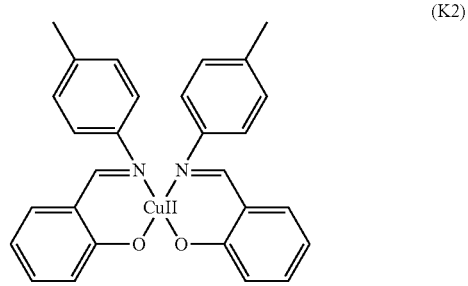

(K2)

3) Copper(II)-bis(N,N'-4-butyl)disalicylaldiminate
(K3 Hereinafter)

Salicylaldehyde (S) and butylamine (B) condense in the presence of the copper salt in ethanolic solution without protic catalysis to give the aldimine derivative which, after formation, is introduced immediately into the ligand sphere of the copper:

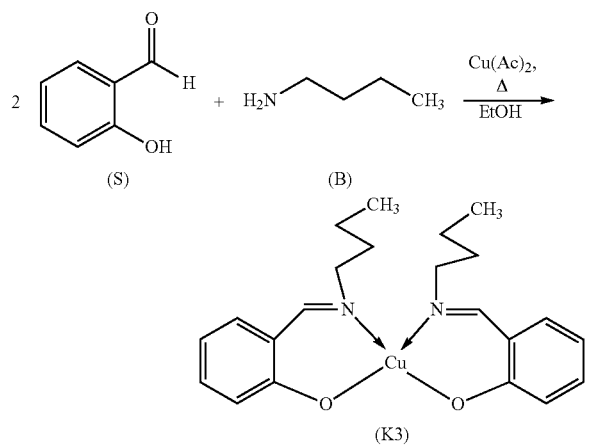

K3 has a melting point of 79° C. and sublimes at 79° C. to 81° C. The yield is 19.8 g (corresponding to 70%).

The working examples which follow show various electrical and optical properties of the p-dopants K1 to K3.

4) A 200 nm-thick layer of the hole conductor 1-TNATA (4,4',4"-tris(N-(1-napthyl)-N-phenylamino)triphenylamine) is deposited onto an ITO electrode 20 by thermal vaporization (comparative example M1). A 150 nm-thick aluminum layer serves as the counter electrode 90. In three further experiments, the dopant K1 is introduced by doping in concentrations of 2% (K1-2), 5% (K1-5) and 10% (K1-10) relative to the vaporization rate in 1-TNATA, the matrix material.

Figure 2:
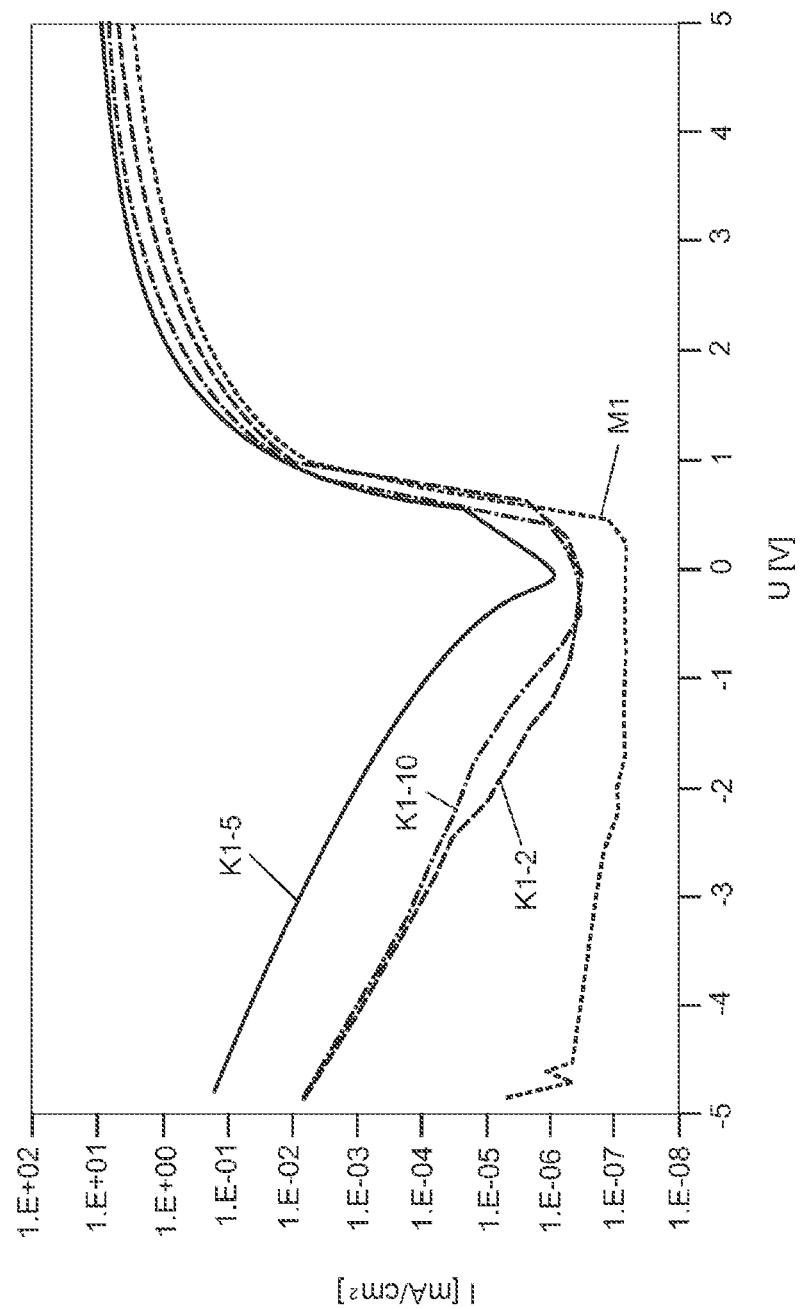
FIG. 2 shows the IV characteristics of doped hole transport layers in a first embodiment.

A component of size 4 $mm^2$ gives the respective current-voltage characteristics (IV characteristics) shown in FIG. 2. The current I in [$mA/cm^2$] is plotted against the voltage U in [V]. The component with concentration 2% gave the characteristic labeled K1-2, the component with concentration 5% the characteristic marked K1-5, and the component with concentration 10% the characteristic labeled K1-10. For comparison, the IV characteristic of the pure matrix material is shown, labeled M1.

For all concentrations, it is possible to show that the doping has an effect on the IV characteristic. For all 3 concentrations, a rise in the current densities is found compared to the comparative example M1. In this context, it is additionally found that the doping effect depends on the dopant concentration and attains the highest current density at concentration 5%. No ideal symmetric behavior of the characteristic is observed, but an increase in the current density by a few orders of magnitude is achieved even in the negative voltage range, which shows that injection of holes from the aluminum cathode 90 is also possible.

5) Conductive substrates are coated with the doped materials (M1, K1-2, K1-5 and K1-10) mentioned in example 4. These conductivity substrates were used to produce a total of 9 components of various dimensions. For the determination of conductivity, this rules out any dependence of the effects measured on the thickness and area of the components. For this substrate type, it is not necessary to apply an aluminum counterelectrode.

The components thus produced give rise to the conductivity of the layer having the following specific values for the dopant concentrations selected here:
M1: 9.10e−9 S/m
K1-2: 1.81e−6 S/m
K1-5: 1.86e−6 S/m
K1-10: 2.15e−6 S/m.

Figure 3:
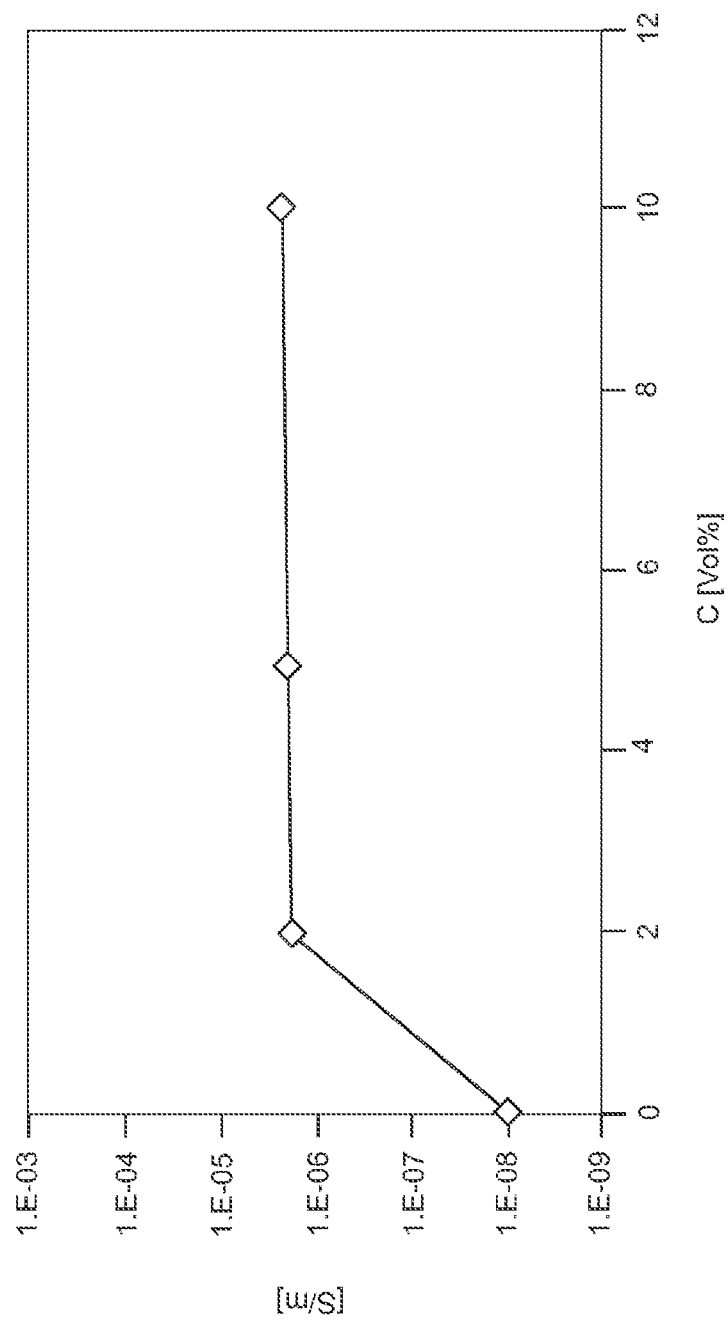
FIG. 3 shows conductivities of doped hole transport layers in a first embodiment as a function of the dopant concentration.

FIG. 3 shows the measured conductivities L in [S/m] against the dopant concentration C in [% by volume]. At the same time, the profile shown also confirms the characteristics shown in FIG. 2. The conductivity attains its maximum at concentration 5%, the measured conductivities of 2% to 10% having very similar and almost constant conductivities. For a possible application, this gives rise to a relatively large processing window for the dopant concentration, without influencing the electrical conductivity thereof.

6) The materials produced in example 4 (M1, K1-2, K1-5 and K1-10) are each deposited on a quartz glass sheet. These samples do not have any electrical contacts and serve merely for measurement of absorption, emission and reflection spectra of the individual layers.

Figure 4:
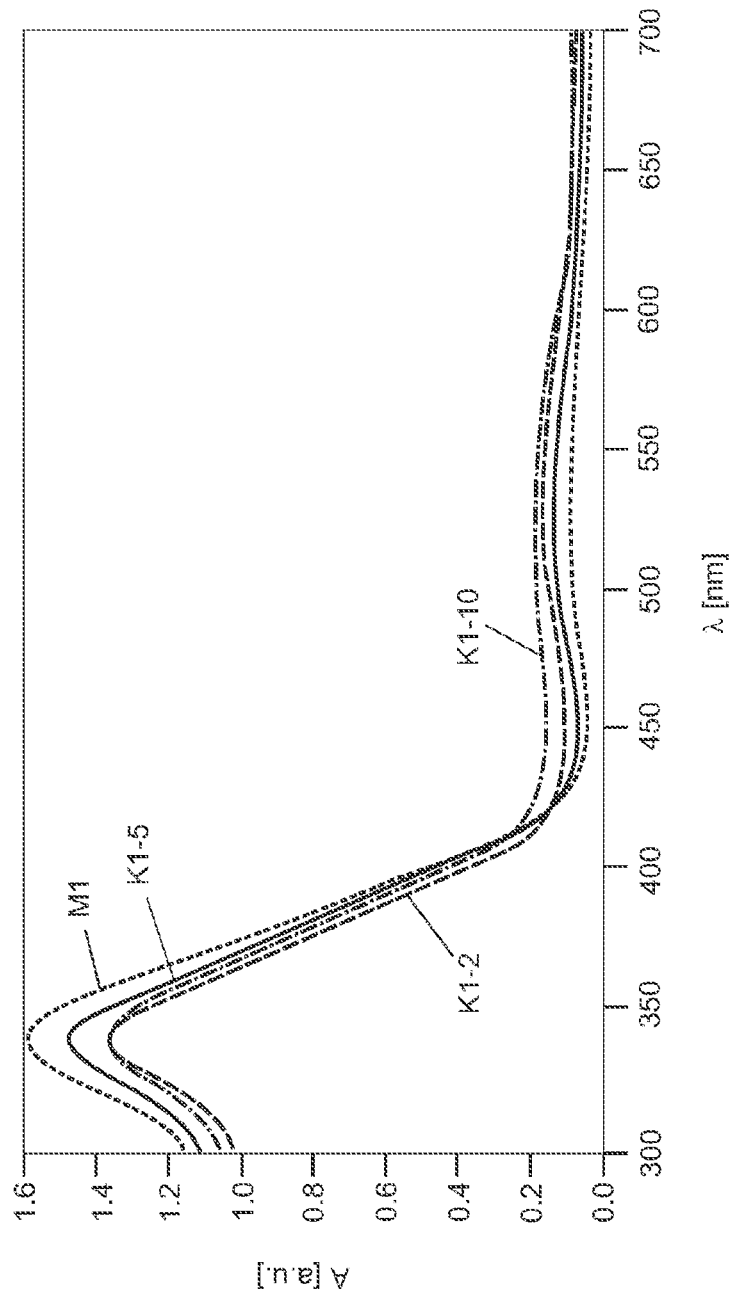
FIG. 4 shows absorption spectra of the doped hole transport layers in the first embodiment.

The absorption spectra according to FIG. 4 (the absorption A in [a.u.] is plotted here against the wavelength λ in [nm]) show that the absolute absorption at the absorption maximum at wavelength 340 nm drops in the case of the doped samples compared to the undoped comparative example M1. The absolute drop here for K1-2 and K1-10 is at about the same level, while the drop at dopant concentration 5% (K1-5) is smaller.

The absorption of the matrix material 1-TNATA below 400 nm is thus lowered by the forming of the doped layer and the associated formation of a charge-transfer complex.

At the same time, however, there is a rise in the absorption between 440 nm and 600 nm. This likewise shows the formation of a charge-transfer complex and successful doping. At the same time, it is additionally found that the rise in absorption in this region increases with rising dopant concentration. The absorption spectrum therefore fits very well with the results of the conductivity measurements and the IV characteristics, which are shown in FIGS. 3 and 2.

For the visible wavelength range from 400 to 700 nm, the absorption in the blue to green wavelength range thus rises, as a result of which the layers doped with the p-dopant appear reddish to the human eye.

Figure 5:
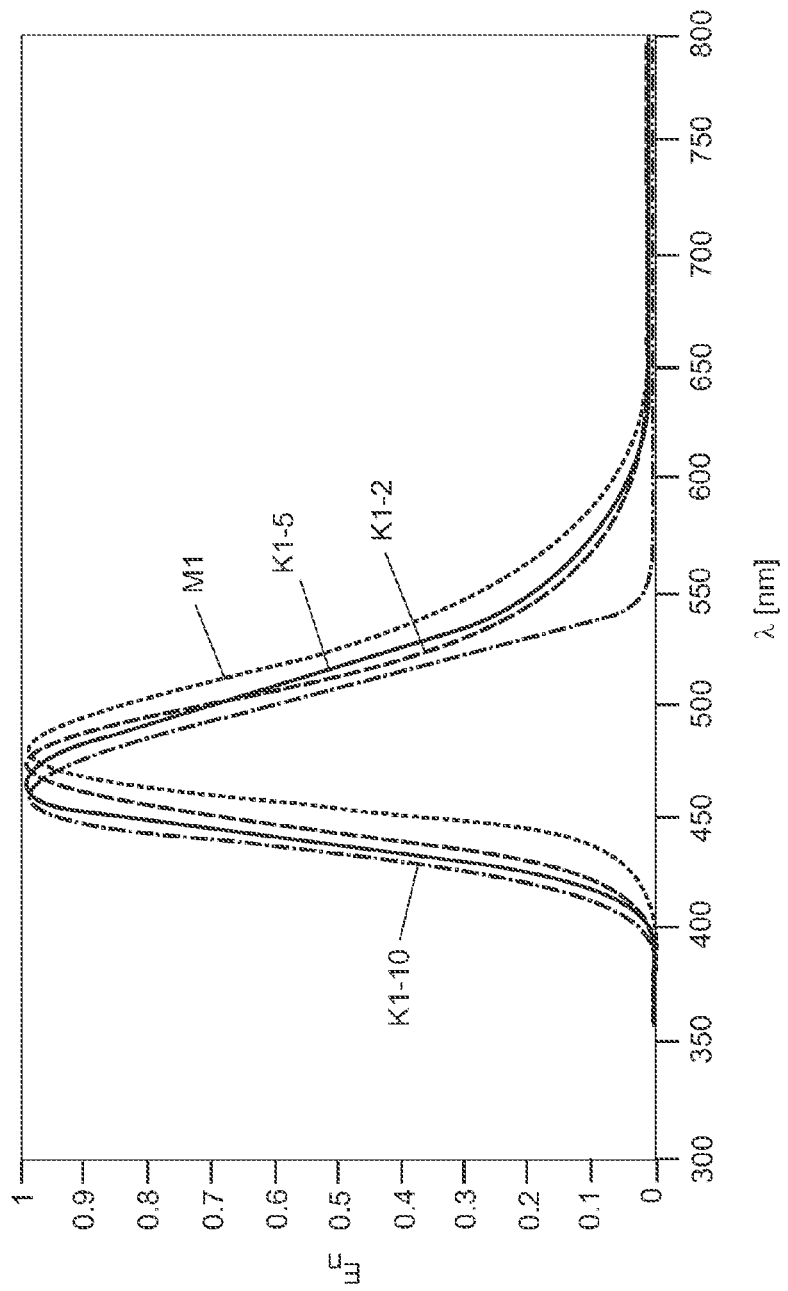
FIG. 5 shows photoluminescence spectra of the doped hole transport layers in the first embodiment.

FIG. 5 shows the photoluminescence (PL) spectra of the abovementioned samples. The normalized emission $E_n$ is plotted against the wavelength $\lambda$ in [nm].

The comparison of the PL spectra of undoped 1-TNATA (M1) and K1-doped 1-TNATA (K1-2, K1-5, K1-10) shows that the emission at a wavelength of 487 nm customary for 1-TNATA moves through 477 nm for dopant concentration 2% to 463 nm for dopant concentrations 5% and 10%. The basic emission profile is maintained, with a decrease in the absolute emission of 1-TNATA when doped with K1.

Figure 6:
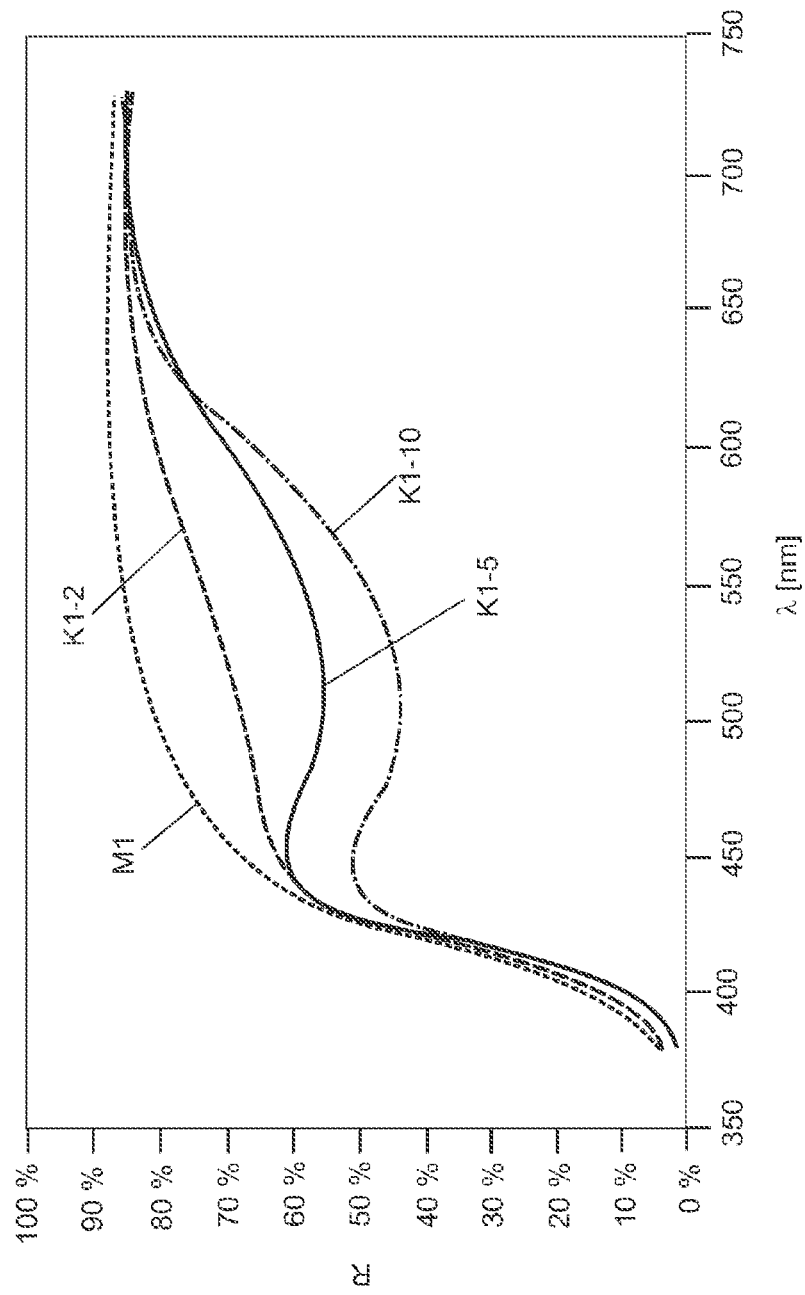
FIG. 6 shows reflection spectra of the doped hole transport layers in the first embodiment.

The reflection spectra in FIG. 6, in which the reflection R is plotted against the wavelength $\lambda$ in [nm], likewise show the information already shown by the absorption spectrum in FIG. 4. With rising dopant concentration, the reflection falls in the blue-green wavelength range (440 to 600 nm) and is maintained in the red range. Again, there is dependence on the dopant concentration, and the reflection in the blue-green region decreases ever further with rising dopant concentration. This can also be seen visually in the substrates, the shade of which becomes ever darker and redder to the human eye with rising concentration.

7) A 200 nm-thick layer of the hole conductor HTM-014 (a triarylamine derivative from Merck) is deposited on an ITO electrode 20 by thermal vaporization (M2). A 150 nm-thick aluminum layer served as the counter electrode 90. In three further experiments, the dopant K2 was doped into the matrix material in concentrations of 5% (K2-5), 15% (K2-15) and 30% (K2-30) relative to the vaporization rate.

Figure 7:
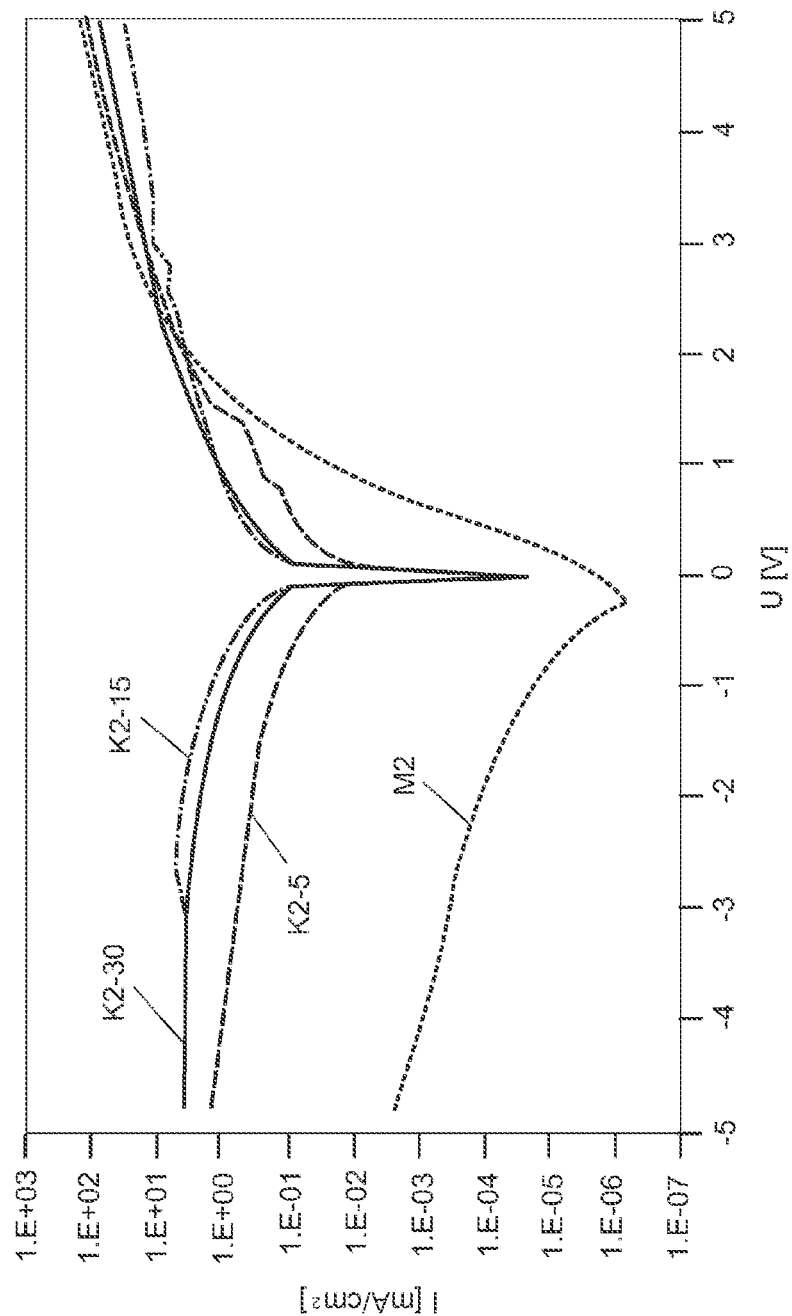
FIG. 7 shows IV characteristics of doped hole transport layers in a second embodiment.

A component of size 4 mm$^2$ gives the respective current-voltage characteristics (IV characteristic) shown in FIG. 7. The component with concentration 5% gave the characteristic labeled K2-5, the component with concentration 15% the characteristic marked K2-15, and the component with concentration 30% the characteristic labeled K2-30.

For all concentrations, it is possible to show that the doping has an effect on the IV characteristic. For all 3 concentrations, a rise in the current densities within the range from −5 V to 1.5 V is found compared to the reference component M2 composed of pure HTM014. In this context, it is additionally found that the doping effect is dependent on the dopant concentration and attains the highest current density at concentration 15%. No ideal symmetric behavior of the characteristic is observed, but an increase in the current density by a few orders of magnitude is achieved even in the negative voltage range, which shows that injection of charge carriers from the aluminum cathode 90 is also possible.

The maximum current density does not increase compared to the reference component (M2), but there is a reduction in voltage or increase in current density, particularly for small voltages in the range of 0 V to 1 V.

8) The materials produced in example 7 (M2, K2-5, K2-15 and K2-30) are coated onto conductive substrates. These conductive substrates were used to produce a total of 9 components of different dimensions. In this way, it is concluded, with regard to the determination of conductivity, that the effects measured are dependent on the thickness and size of the components. For this substrate type, it is not necessary to apply an aluminum counterelectrode.

The components thus produced give rise to the conductivity of the layer having the following specific values for the dopant concentrations selected here:

K2-5: 3.45e−6 S/m
K2-15: 1.06e−6 S/m
K2-30: 1.45e−6 S/m

Figure 8:
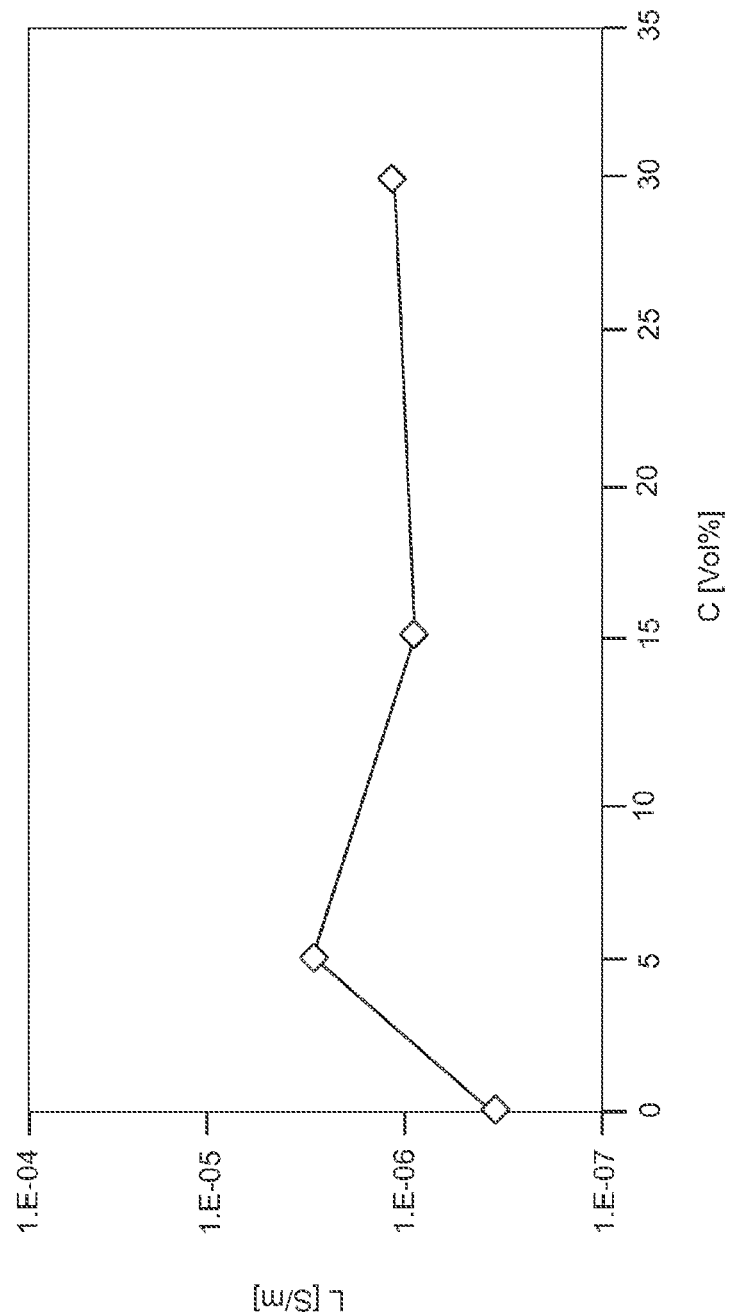
FIG. 8 shows conductivities of a second embodiment of doped hole transport layers as a function of the dopant concentration.

FIG. 8 shows the measured conductivities L in [S/m] against the dopant concentration C in % by volume. The profile shows an improvement in the conductivity by one to two orders of magnitude. The maximum here is at a concentration of 5% (K2-5), and the conductivities for 15% and 30% (K2-15 and K2-30) are very similar taking account of process and measurement variations and hence there is almost a constant conductivity. For a possible application, this gives rise to a relatively large processing window for the dopant concentration, without influencing the electrical conductivity thereof.

9) The layers produced in example 7 (M2, K2-5, K3-15 and K2-30) are additionally each deposited on a quartz glass sheet. These samples do not have any electrical contacts and serve merely for measurement of absorption, emission and reflection spectra of the individual layers. For this purpose, in addition, a sample having the same thickness (200 nm) of pure K2 (K2-100) was produced, in order also to determine the optical data thereof.

The absorption spectra (FIG. 9, absorption A in [a.u.] against the wavelength $\lambda$ in [nm]) show that there is a drop in the absolute absorption A at the absorption maximum at wavelength 380 nm. The absolute drop here for concentration 5% (K2-5) and 15% (K2-15) is at about the same level, while the drop for dopant concentration 30% (K2-30) is greater. The pure 100% layer (K2-100) has a lower concentration again.

The absorption of the pure matrix material (M2) below 400 nm is thus lowered by the forming of the doped layer and the associated formation of a charge-transfer complex. At the same time, however, there is a rise in the absorption A between 440 nm and 550 nm for the doped layers. This likewise shows the formation of a charge-transfer complex and successful doping. At the same time, it is additionally found that the rise in absorption within this range increases with rising dopant concentration. The absorption spectrum therefore fits very well with the results of the conductivity measurements and of the IV characteristics from FIGS. 8 and 7.

For the visible wavelength range from 400 to 700 nm, the absorption in the blue to green wavelength range thus rises, as a result of which the layers appear reddish to the human eye. The absorption of the pure K2 layer (K2-100) is higher than the doped and undoped layers over the entire visible wavelength range.

Figure 10:
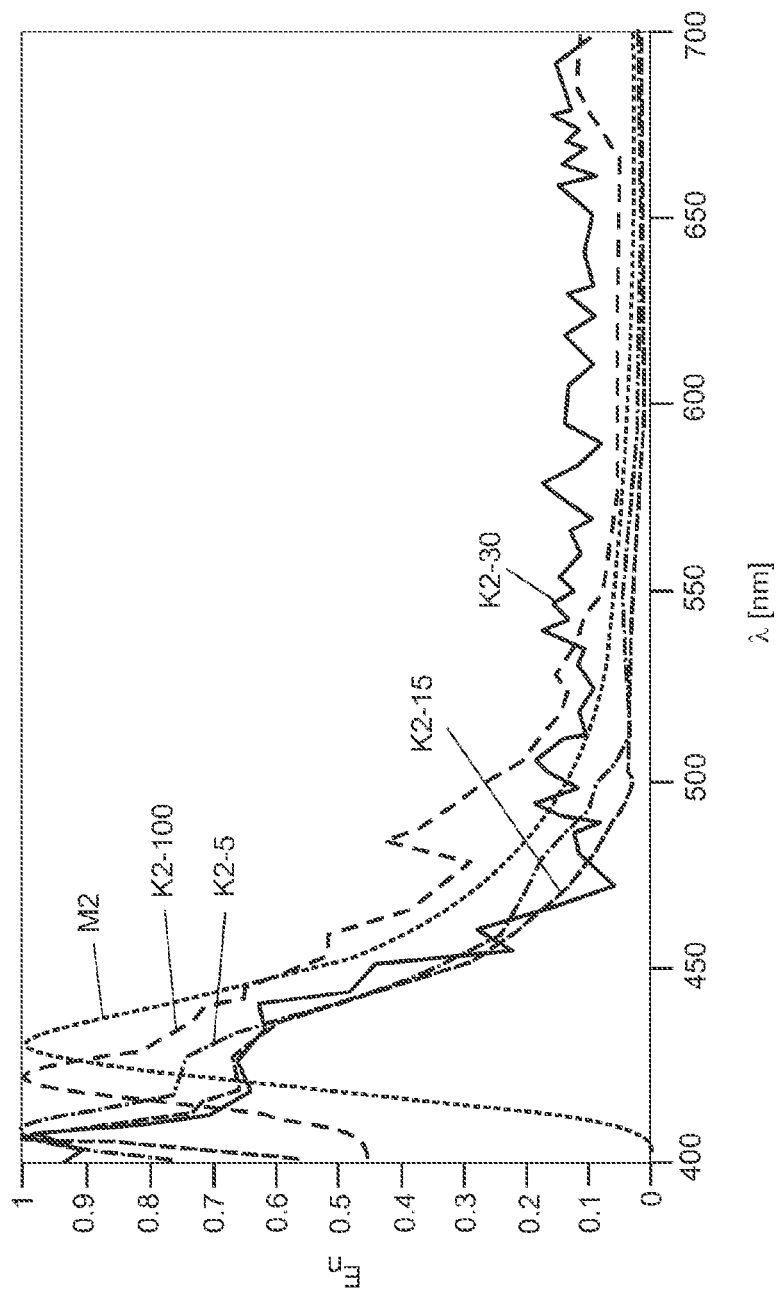
FIG. 10 shows photoluminescence spectra of the doped hole transport layers in the first embodiment.

The comparison of the photoluminescence spectra in FIG. 10, in which the normalized emission $E_n$ is plotted against the wavelength $\lambda$ in [nm], of undoped matrix material (M2) and K2-doped matrix material shows that the emission at a wavelength of 432 nm customary for the matrix material moves to 406 to 408 nm for all doped layers. The basic emission profile is maintained, with a decrease in the absolute emission of HTM-014 when doped with K2. In addition, a shoulder at 432 nm forms for all doped layers. The behavior of the K2-30 sample in the range of 480 to 700 nm is not a property of the material, but a measurement artefact caused by the low overall emission of this sample. The absolute emissions of the layers are not taken into account here; instead, each emission spectrum is normalized.

The pure K2 layer (K2-100) has its emission maximum at 423 nm with a secondary maximum at 485 nm.

Figure 9:
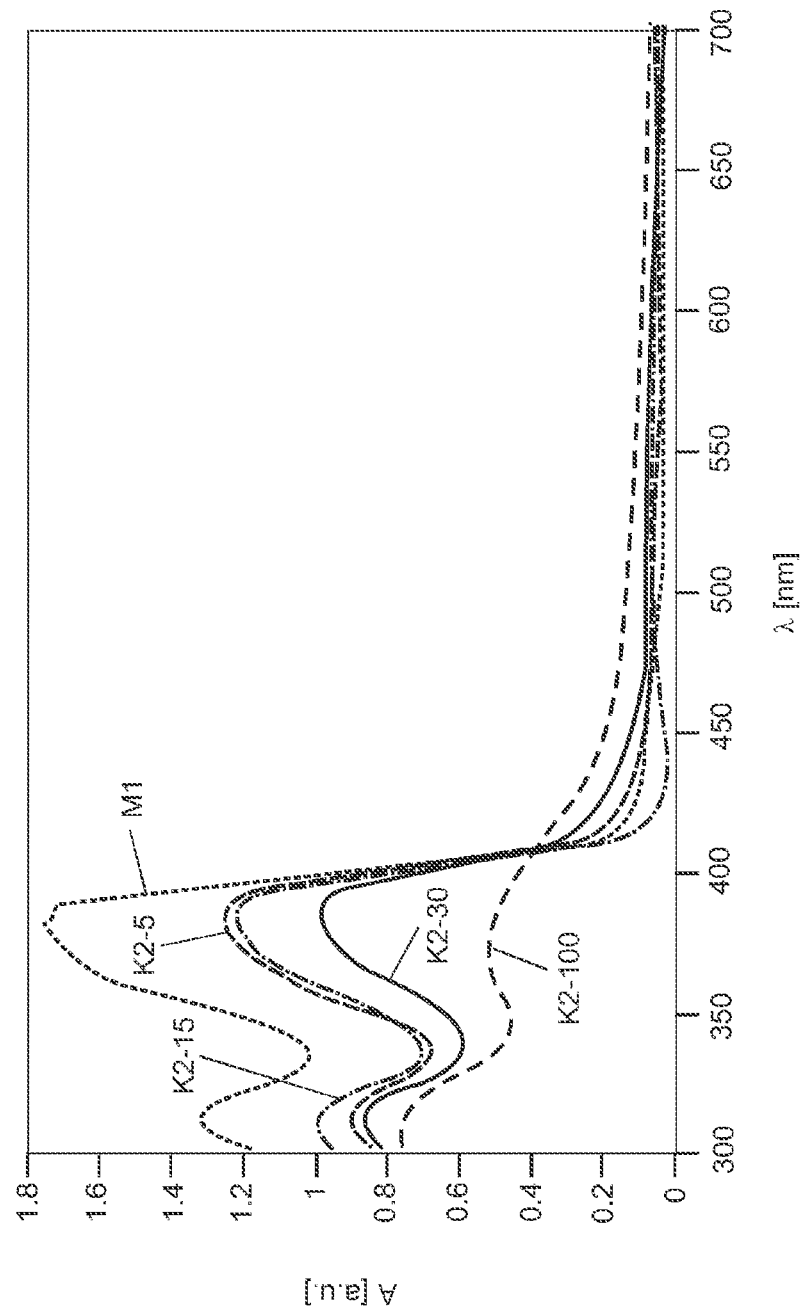
FIG. 9 shows absorption spectra of the doped hole transport layers in the second embodiment.
Figure 11:
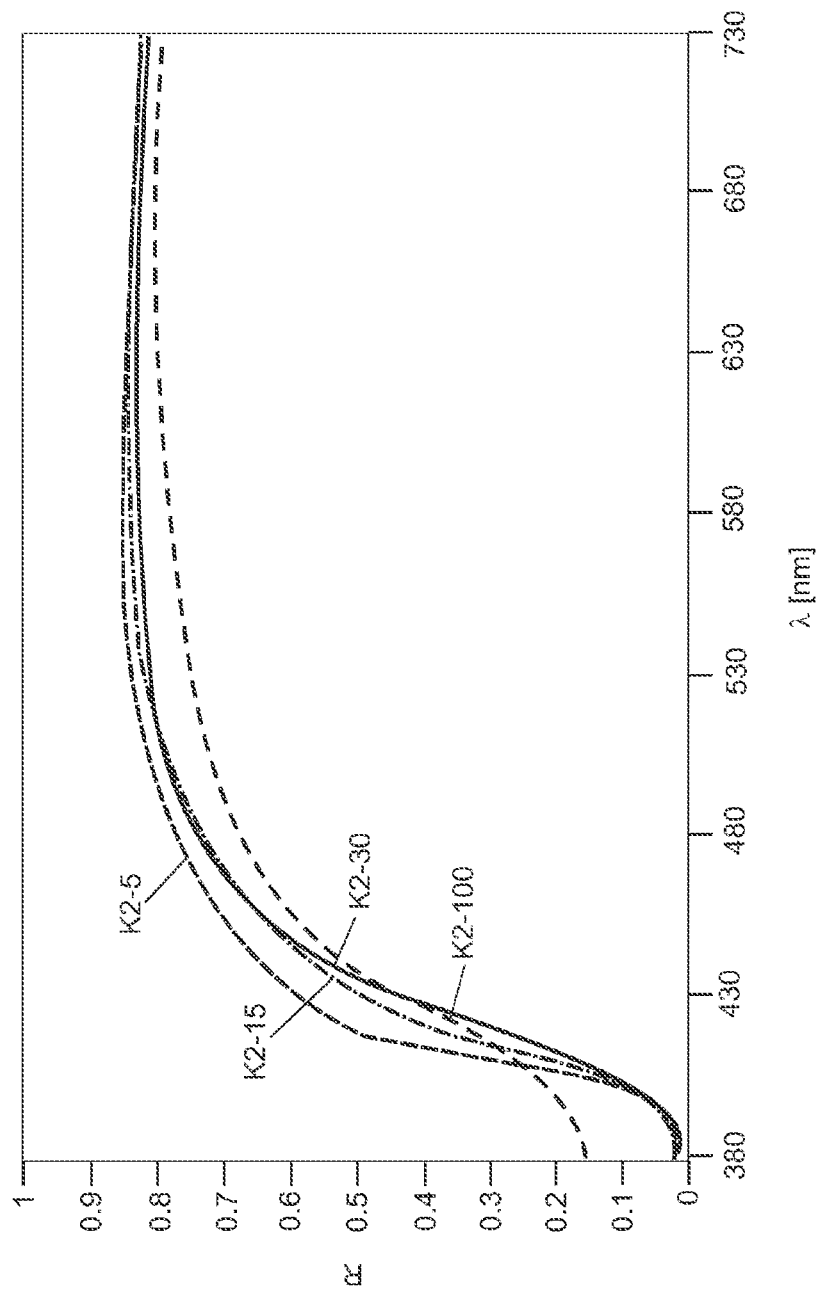
FIG. 11 shows reflection spectra of the doped hole transport layers in the first embodiment.

The reflection spectra shown in FIG. 11 (reflection R against wavelength λ in [nm]) likewise show the information already shown by the absorption spectrum in FIG. 9. With rising dopant concentration, there is a drop in the reflection in the blue-green wavelength range (400 to 580 nm), and it is maintained within the red range. Again, the dependence on the dopant concentration is present, and the reflection in the blue-green region decreases ever further with rising dopant concentration. This can also be visualized in the substrates, the hue of which becomes ever darker to the human eye with rising concentration. It is likewise confirmed that the pure p-dopant layer (K2-100), for wavelengths below 400 nm, has a lower absorption A and hence higher reflection R. Over the entire wavelength range and particularly in the range of 450 nm to 630 nm, the reflection is much lower than that of the doped layers.

Examples 10) to 13) which follow show further working examples for the p-dopants:

10) A further example of a p-dopant which can be prepared by the abovementioned process from 3,5-difluorosalicylaldehyde and pentafluoroaniline is shown in its cis and trans forms in the formulae Va and Vb:

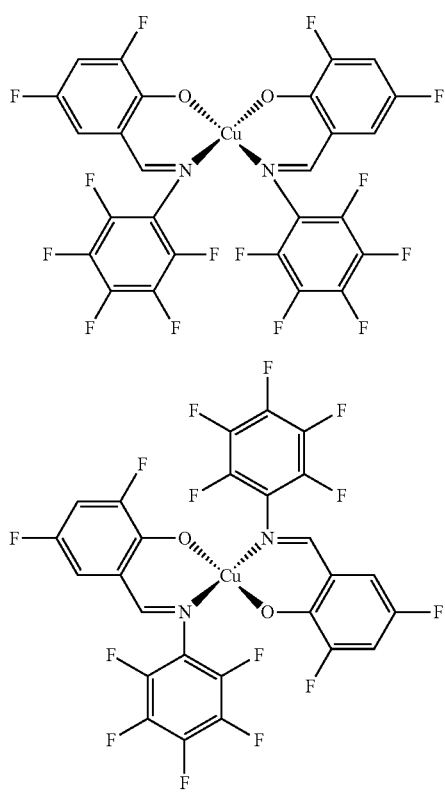

11) Alternatively to pentafluoroaniline in example 13), it is also possible to use the tetrafluoroaniline derivatives 2,3,4,5-tetrafluoroaniline, 2,3,4,6-tetrafluoroaniline or 2,3,5,6-tetrafluoroaniline, or the tri-, di- or monofluoroaniline derivatives.

12) Further aniline derivatives which can be used in the abovementioned process are trifluoromethyl groups or derivatives additionally having fluorine substituents, for example, 2-fluoro-3-(tri-fluoromethyl)aniline, 2-fluoro-4-(trifluoromethyl)-aniline, 2-fluoro-5-trifluoromethylaniline, 2-fluoro-6-(trifluoromethyl)aniline, 3-fluoro-2-(trifluoromethyl)-aniline, 3-fluoro-4-(trifluoromethyl)aniline, 3-fluoro-5-(trifluoromethyl)aniline, 4-fluoro-2-(trifluoromethyl)aniline, 4-fluoro-3-(trifluoromethyl)aniline, 5-fluoro-2-(trifluoromethyl)aniline.

13) The salicylaldehydes used for production of the p-dopant may also be 4-(trifluoromethyl)salicylaldehyde or 4-(trifluoromethoxy)salicylaldehyde.

The invention is not restricted by the description of the working examples; instead, the invention encompasses every novel feature and every combination of features, which especially includes every combination of features in the claims, even if this feature or this combination itself is not specified explicitly in the claims or working examples.

What is claimed is:

1. An organic electronic component, comprising:
   a substrate;
   a first electrode arranged on the substrate;
   at least one organic functional layer arranged on the first electrode, the at least one organic functional layer comprising a matrix material into which a p-dopant has been introduced; and
   a second electrode arranged on the at least one organic functional layer,
   wherein the p-dopant comprises a copper complex having a copper cation and at least two ligands,
   wherein each ligand has a benzene unit comprising six carbon atoms,
   wherein, with respect to each ligand, an oxygen is bound as a substituent to one of the six carbon atoms of the benzene unit, with the oxygen and the benzene unit together forming an aryloxy group, and an adjacent carbon atom of the six carbon atoms of the benzene unit is substituted with a substituent that, together with the benzene unit, forms an iminium group,
   wherein the at least two ligands are coordinated to the copper cation, so that the copper complex has a trans-structure, and
   wherein the at least one organic functional layer is hole-conducting.

2. The component according to claim 1, wherein the aryloxy group and the iminium group of one of the at least two ligands are a salicylaldiminate group.

3. The component according to claim 1, wherein the copper cation is in an II oxidation state.

4. The component according to claim 1, wherein the matrix material is a hole transport material comprising organic small molecules, polymers or mixtures thereof.

5. The component according to claim 4, wherein the hole transport material is N,N'-di-[(1-naphthyl)-N,N'-diphenyl]-1,1'-biphenyl)-4,4'-diamine.

6. The component according to claim 1, wherein each molecule of the p-dopant is coordinated by at least one molecule of the matrix material.

7. The component according to claim 1, wherein the p-dopant is present in the matrix material in a concentration of 0.1 to 50% by volume relative to the volume of the matrix material.

8. The component according to claim 1, wherein the component is a field-effect transistor, a solar cell, a photodetector, an optoelectronic component, a light-emitting diode or a display.

9. The component according to claim 1, wherein the at least one organic functional layer is a hole transport layer or a hole-conducting layer of a charge-generating layer sequence.

10. A method for producing a p-dopant for an organic electronic component, the method comprising:

synthesizing at least two ligands and, simultaneously, complexing a copper cation with the at least two ligands;

wherein each ligand of the at least two ligands has a benzene unit comprising six carbon atoms, wherein, with respect to each ligand, an oxygen is bound as a substituent to one of the six carbon atoms of the benzene unit, with the oxygen and benzene unit together forming an aryloxy group, and an adjacent carbon atom of the six carbon atoms of the benzene unit is substituted with a substituent that, together with the benzene unit, forms an iminium group, and wherein the at least two ligands are coordinated to the copper cation, so that the copper complex has a trans-structure.

* * * * *